United States Patent
Dabdoub

(10) Patent No.: US 7,420,081 B2
(45) Date of Patent: Sep. 2, 2008

(54) METHODS FOR SYNTHESIZING PHOSPHONIC COMPOUNDS AND COMPOUNDS THEREOF

(75) Inventor: Atif M. Dabdoub, Atlanta, GA (US)

(73) Assignee: Unichem Technologies, Inc., Atlanta, GA (US)

( * ) Notice: Subject to any disclaimer, the term of this patent is extended or adjusted under 35 U.S.C. 154(b) by 0 days.

(21) Appl. No.: 11/743,947

(22) Filed: May 3, 2007

(65) Prior Publication Data

US 2007/0287858 A1    Dec. 13, 2007

Related U.S. Application Data

(63) Continuation of application No. 10/886,406, filed on Jul. 7, 2004.

(51) Int. Cl.
*C07F 9/30*    (2006.01)

(52) U.S. Cl. ............................................. 562/8; 562/20

(58) Field of Classification Search ........................ None
See application file for complete search history.

(56) References Cited

U.S. PATENT DOCUMENTS

| | | | |
|---|---|---|---|
| 2,365,466 A | 12/1944 | Hamilton | |
| 2,632,768 A | 3/1953 | Coover et al. | |
| 3,613,788 A | 10/1971 | Kautsky | |
| 3,619,427 A | 11/1971 | Kautsky | |
| 3,738,937 A | 6/1973 | Kautsky | |
| 3,887,340 A | 6/1975 | Hsu et al. | |
| 4,132,526 A | 1/1979 | Schwarz et al. | |
| 4,190,615 A | 2/1980 | Becker | |
| 4,201,669 A | 5/1980 | Becker et al. | |
| 4,237,005 A | 12/1980 | Becker | |
| 4,342,733 A | 8/1982 | Steelhammer et al. | |
| 4,387,027 A | 6/1983 | May et al. | |
| 4,409,192 A | 10/1983 | Lichtner et al. | |
| 4,446,028 A | 5/1984 | Becker | |
| 4,446,046 A | 5/1984 | Becker | |
| 4,900,451 A | 2/1990 | Michael et al. | |
| 4,997,523 A | 3/1991 | Pease | |
| 5,180,498 A | 1/1993 | Chen et al. | |
| 5,350,536 A | 9/1994 | Chen et al. | |
| 5,519,102 A | 5/1996 | Cady et al. | |
| 5,596,130 A | 1/1997 | Wright et al. | |

OTHER PUBLICATIONS

Patent abstract of Japan and machine generated English translation of JP 05-086081, published Jun. 4, 1993.*

G. Ohms, G. Grobman, B. Schwab, H. Schieffer,Synthesis and 31P and 13C NMR Studies of Pyrophosphonic Acids, Phosphorus, Sulfur,and Silicon, 1992, pp. 78-89,vol. 68, Gordon and Breach Sciences Publishers S.A., United Kingdom.

* cited by examiner

*Primary Examiner*—Rosalynd Keys
(74) *Attorney, Agent, or Firm*—Gardner Groff Greenwald & Villanueva, P.C.

(57) ABSTRACT

Described herein are methods for producing phosphonic compounds and compounds thereof.

22 Claims, No Drawings

METHODS FOR SYNTHESIZING PHOSPHONIC COMPOUNDS AND COMPOUNDS THEREOF

IN THE CROSS-REFERENCE TO RELATED APPLICATIONS

This application is a continuation of U.S. application Ser. No. 10/886,406, filed Jul. 7, 2004, which is hereby incorporated herein by reference in its entirety for all purposes.

BACKGROUND

Polyphosphonic acids have numerous applications in industry. For example, polyphosphonic acids can be used as corrosion inhibition agents in cooling water and boiler water systems (U.S. Pat. Nos. 4,446,046 and 4,201,669) and inhibitors of fouling deposit formation on jet engine components during the combustion of finished turbine combustion fuel oils (U.S. Pat. No. 5,596,130). One approach to the synthesis of polyphosphonic acids involves the radical polymerization of unsaturated phosphonic acid monomers (U.S. Pat. Nos. 4,201,669, 4,446,046 and 5,519,102).

An unsaturated phosphonic acid monomer that has received considerable attention is isopropenylphosphonic acid, which has the formula $H_2C=C(CH_3)(PO_3H_2)$, which is referred to herein as "IPPA." IPPA is currently prepared by reacting $PCl_3$ with acetic acid and acetone (U.S. Pat. No. 4,446,046). This process, however, possesses numerous disadvantages. First, $PCl_3$ is an extremely corrosive, hazardous, and toxic chemical. It requires special handling starting from transportation to storage to delivery to reactors. Any release of $PCl_3$ would require immediate evacuation. Second, the process produces HCl and acetyl chloride, which are also very hazardous and volatile by-products. The process is further complicated since these by-products come out as a mixture and have to be scrubbed by water. This dilution magnifies the quantity of these by-products and leaves a mixture of HCl and acetyl chloride in water. Finally, $PCl_3$ and the reaction by-products are very corrosive and require special equipment such as glass-lined reactors, condensers, scrubbers, collection tanks, etc. The use of $PCl_3$ requires the use of equipment that is non-reactive with chlorides. Thus, equipment composed of other materials such as stainless steel cannot be used in the production of IPPA, which reduces large-scale commercial production capabilities.

Thus, it is desirable to have a process that produces phosphonic compounds that are precursors to polyphosphonic compounds on large scale that do not require the use of $PCl_3$ and/or specialized equipment such as glass-lined reactors and accessories, etc. It would also be advantageous not to produce toxic, corrosive, and hazardous by-products during the synthesis of the phosphonic compound. Finally, it would be desirable to produce phosphonic compounds on commercial scale without special equipment such as glass-lined reactors. The methods described herein accomplish these goals.

SUMMARY

Described herein are methods for producing phosphonic compounds and compounds thereof.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$-$R^9$ used throughout the application are the same variables as previously defined unless stated to the contrary.

The term "alkyl group" as used herein is a branched- or straight-chain saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphoris. The aryl group can be substituted or unsubstituted. The aryl group can be substituted with one or more groups including, but not limited to, allyl, alkynyl, alkenyl, aryl, halide, nitro, amino, ester, ketone, aldehyde, hydroxy, carboxylic acid, alkoxy, or $SO_2R$ or $S(O)_2OR$, where R can be hydrogen or an alkyl group described above. The aryl group also includes aralkyl such as, for example, benzyl. The aryl group of the aralkyl group can be substituted with one or more groups listed above.

The term "protecting group" as used herein is a group that can be chemically bound to an oxygen atom, and subsequently removed (either chemically, in-vitro, or in-vivo) from the oxygen atom by predictable methods. Examples of many of the possible protective groups can be found in *Protective Groups in Organic Synthesis* by T. W. Green, John Wiley and Sons, 1981, which is incorporated herein by reference in its entirety.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Described herein are methods for producing phosphonic compounds. In one aspect, a method for making the phosphonic compound involves reacting compounds I, II, and III

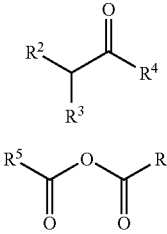

wherein $R^1$-$R^7$ can be, independently, hydrogen, an alkyl group, a cycloalkyl group, a heterocycloalkyl group, an aryl group, a heteroaryl group, a protecting group, or a combination thereof.

The selection of compounds I, II, and III will vary depending upon reaction conditions and the desired phosphonic compound to be produced. In one aspect, with respect to compound I, $R^1$ and $R^7$ can be, independently, hydrogen, an alkyl group, a cycloalkyl group, a heterocycloalkyl group, an aryl group, a heteroaryl group, a protecting group, or a combination thereof. In another aspect, $R^1$ and $R^7$ in formula I are hydrogen. This compound ($H_3PO_3$) is referred to as phosphorous acid or phosphonic acid, which is a stable powder and much easier to handle when compared to $PCl_3$. Indeed, phosphonic acid is more environmentally friendly and substantially more stable than $PCl_3$, and can be transported in bags to storage or to the reactor. In a further aspect, $R^1$ and $R^7$ can be, independently, methyl, ethyl, propyl, isopropyl, butyl, pentyl, or hexyl. In the case when $R^1$ and $R^7$ are methyl, the compound is dimethyl hydrogen phosphite. In another aspect, $R^1$ and $R^7$ can be aryl groups such as phenyl or cycloalkyl groups.

In one aspect, $R^2$-$R^4$ of formula II can be, independently, hydrogen, an alkyl group, a cycloalkyl group, a heterocycloalkyl group, an aryl group, a heteroaryl group, a protecting group, or a combination thereof. In one aspect, $R^2$ and $R^3$ in formula II is hydrogen. In another aspect, $R^2$ and $R^3$ in formula II are hydrogen and $R^4$ can be a branched- or straight-chain alkyl group such as, for example, methyl, ethyl, propyl, isopropyl, butyl, pentyl, or hexyl. In another aspect, $R^2$ and $R^3$ in formula II are hydrogen and $R^4$ can be an aryl group or a heteroaryl group such as, for example, a phenyl group. In another aspect, compound II can be acetone, methylphenyl ketone ($R^2$ and $R^3$ are hydrogen, $R^4$ is phenyl), sulfonated benzyl methyl ketone ($R^2$ and $R^3$ are hydrogen, $R_4$ is $CH_2$—$C_6H_4$-p-$SO_2OH$), or ethanal ($R^2$, $R^3$, and $R^4$ are hydrogen).

In one aspect, $R^5$ and $R^6$ of formula III can be, independently, hydrogen, an alkyl group, a cycloalkyl group, a heterocycloalkyl group, an aryl group, a heteroaryl group, a protecting group, or a combination thereof. In one aspect, $R^5$ and $R^6$ can be, independently, a branched- or straight-chain alkyl group such as, for example, methyl, ethyl, propyl, isopropyl, butyl, pentyl, or hexyl. In another aspect, formula III can be acetic anhydride, propionic anhydride, or butyric anhydride.

The reaction for producing the phosphonic compound can optionally be performed in the presence of a catalyst. In one aspect, the catalyst can facilitate the formation of the phosphonic compound. In another aspect, a compound having the formula $R^8COOH$, wherein $R^8$ can be $C_1$-$C_8$ branched- or straight-chain alkyl such as, for example, methyl, ethyl, propyl, isopropyl, butyl, pentyl, or hexyl can be used as the catalyst. Not wishing to be bound by theory, it is believed that the catalyst can solubilize one or more intermediates that ultimately lead to the production of the phosphonic compound. The catalyst can be added to the reaction as a separate component or can be produced in situ. For example, when compound I is phosphorous acid, compound II is acetone, and compound III is acetic anhydride, glacial acetic acid is produced during the reaction. In this example, the glacial acetic acid can be isolated and sold commercially or used in future reactions.

The amount of components I, II, and III can vary depending upon the compounds selected and reaction conditions. In one aspect, the amount of component I is from 10% to 25%, 15% to 25%, or 15% to 20% by weight, the amount of component II is from 10% to 25%, 15% to 25%, or 15% to 20% by weight, and the amount of component III is from 10 to 70%, 20% to 60%, or 30% to 60%, by weight, wherein the sum of components I-III is 100%. When a catalyst is used, in one aspect, the amount of catalyst is from 1% to 50%, 5% to 40%, 5% to 30%, or 5% to 25% by weight, wherein the sum of components I-III and the catalyst is 100%. Components I-IIII and the optional catalyst can be added to one another in any order using the methods described herein. This is not the case when $PCl_3$ is used as the starting material. For example, in U.S. Pat. No. 4,446,046 (the '046 patent), the addition of acetic acid to $PCl_3$ is very dangerous and can be explosive if performed on a large scale. The methods described herein do not use $PCl_3$ and, thus, this is not an issue. In one aspect, components I, III, and the catalyst are mixed with one another followed by the addition of component II.

The reaction time and temperature can vary as well depending upon the selection of components I-III. In one aspect, the reaction temperature can range from 10° C. to 200° C., 10° C. to 190° C., 10° C. to 180° C., 15° C. to 180° C., 15° C. to 170° C., 15° C. to 160° C., or 15° C. to 150° C. Reaction temperatures can fluctuate during the reaction depending upon the selection of components I-III. In one aspect, the rate of addition of component II can vary in order to control the temperature of the reaction.

In one aspect, the reaction time can be from 3 minutes to 10 hours, 10 minutes to 8 hours, 10 minutes to 6 hours, 10 minutes to 4 hours, 10 minutes to 2 hours, 10 minutes to 1 hour, or 30 minutes to 1 hour. The reaction times using the methods described herein are generally much lower than processes that use $PCl_3$. For example, IPPA can be produced from phosphorous acid, acetone, and acetic anhydride with acetic acid as the catalyst in approximately 5 hours. Conversely, if IPPA is produced from $PCl_3$ using the process in the '046 patent, the reaction can take from 25 to 44 hours. One reason why the process in the '046 patent is substantially longer than those described herein is that this process produces HCl and acetyl chloride, which are very toxic and have to be removed by vacuum. HCl and acetyl chloride are the two by-products that are produced when $PCl_3$ is used. As long as $PCl_3$ is being added, these by-products will continue to come out of the reactor and need to be quickly removed under atmospheric pressure or under vacuum. This can jeopardize the reaction, because the starting materials could be volatile and removed from the reaction when the by-products are removed. This is not the case with the present invention, where HCl and acetyl chloride are not produced.

The methods described herein can be performed using readily available equipment and do not require special equipment or handling as required in the process disclosed in the '046 patent. For example, the process disclosed in the '046 patent requires glass-lined reactors, special collection tanks, and scrubbing systems to capture the HCl and acetyl chloride. The methods described herein permit the use of equipment such as, for example, stainless steel reactors, and normal collection tanks and condensers, which are widely available, much less expensive, and easier to operate and maintain. Thus, the methods described herein permit the large-scale production of phosphonic compounds in a commercially practical way.

In one aspect, the phosphonic compounds produced by the methods described have the formula IV

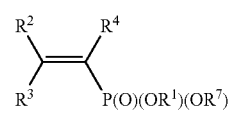

IV wherein $R^1$-$R^4$ and $R^7$ can be, independently, hydrogen, an alkyl group, a cycloalkyl group, a heterocycloalkyl group, an aryl group, a heteroaryl group, a protecting group, or a combination thereof. In one aspect, $R^4$ in formula IV is not an alkyl group. The compounds represented in formula IV are referred to herein as unsaturated phosphonic compounds. In one aspect, $R^2$ and $R^3$ in formula IV can be hydrogen. In another aspect, $R^4$ in formula IV can be an aryl group or a heteroaryl group. In another aspect, $R^1$ and $R^7$ in formula IV can be hydrogen. In another aspect, the compound having the formula IV has the formula $H_2C=C(R^9)(PO_3H_2)$, where $R^9$ can be hydrogen, substituted or unsubstituted phenyl, or substituted or unsubstituted benzyl (e.g., $CH_2C_6H_4$-p-S(O)$_2$OH).

In one aspect, the phosphoric compounds produced by the methods described have the formula VII

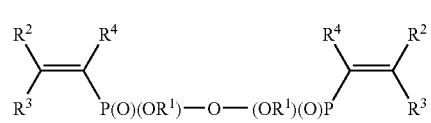

VII wherein $R^1$-$R^4$ can be, independently, hydrogen, an alkyl group, a cycloalkyl group, a heterocycloalkyl group, an aryl group, a heteroaryl group, a protecting group, or a combination thereof. The compounds represented in formula VII are dimers of the compounds having the formula IV. In one aspect, $R^2$ and $R^3$ in formula VII can be hydrogen. In another aspect, $R^4$ in formula VII can be an aryl group or a heteroaryl group. In another aspect, $R^1$ in formula VII can be hydrogen.

In another aspect, the phosphonic compounds produced by the methods described herein have the formula V

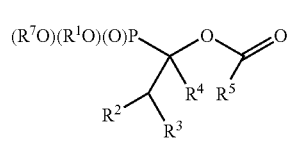

V wherein $R^1$-$R^5$ and $R^7$ can be, independently, hydrogen, an alkyl group, a cycloalkyl group, a heterocycloalkyl group, an aryl group, a heteroaryl group, a protecting group, or a combination thereof. In another aspect, the phosphonic compounds produced by the methods described herein have the formula VI

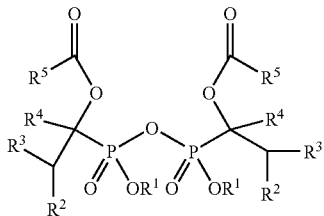

wherein $R^1$-$R^5$ and $R^7$ can be, independently hydrogen, an alkyl group, a cycloalkyl group, a heterocycloalkyl group, an aryl group, a heteroaryl group, a protecting group, or a combination thereof.

Compounds having the formula V and VI are precursors to the unsaturated phosphonic compounds IV and VII, respectively. For example, compound IV is produced if $R^5C(O)OH$ is eliminated from compound V. Similarly, compound VII is produced from compound VI with the loss of two equivalents of $R^5C(O)OH$. Compound VI is the dimer of compound V. Depending upon reaction conditions, the selection of components I-III, and the use of a catalyst, it is possible to produce compounds IV-VII individually or as mixtures of compounds. For example, if excess acetic anhydride (compound III) is used in the reaction, that can promote formation of compound VI.

Any of the unsaturated phosphonic compounds produced herein (compounds IV and VII) can be polymerized using techniques known in the art. For example, the techniques disclosed in the '046 patent, which is incorporated by reference for its teachings as it relates to polymerization chemistry, can be used herein to polymerize compounds having the formula IV and VII.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Isopropenylphosphonic Acid (IPPA)

To a 1.0 L, 3-necked flask equipped with a magnetic stirring bar and an addition funnel, was added 164 g (2.0 moles) of dry, anhydrous phosphorus acid. Acetic anhydride (400 g; 3.9 moles) was added followed by acetic acid (160g; 2.6 moles). The addition funnel was removed, and the flask was then equipped with a heating mantel, magnetic stirrer, thermometer, reflux condenser, and pressure compensated addition funnel. The mixture was stirred at ambient (19° C.) temperature until a clear solution was obtained (10 min; 18° C.). Acetone (140 g; 2.4 moles) was added dropwise through the addition funnel. The temperature started to rise steadily after 3 min of acetone addition and by the time 35 g (0.6 moles after 12 min.) of acetone was added, the temperature had risen from 18° C. to 23° C. The temperature steadily rose to 40° C. by the time 105 g (1.8 moles at 32 min.) of acetone was added. Acetone addition was stopped, and the mixture was allowed to cool for 8 minutes. Acetone addition was resumed at 37° C., and it took 10 minutes to add the rest of the acetone 35 g (0.6 moles). The temperature climbed to 52° C. then completely stopped. Thus, it took 50 minutes to add all the acetone. Optionally, a balance of constant cooling and constant adding of acetone can be maintained. During acetone addition, no acetone was seen refluxing, which indicated that an immediate and stable reaction occurred. Also, the temperature only rose with each further addition of acetone and, the temperature did not rise when acetone addition stopped. The reaction showed extreme control and can be stopped at any point, if necessary. In addition, white oligomers (formula V and VI) were seen temporarily The above mixture was allowed to stir at 50 to 60° C. (low heat was occasionally applied to maintain temperature) for one hour. Moderate heat was then applied, and the temperature was allowed to steadily rise to 100° C.

At this point, a reflux condenser was replaced by an adapter, a thermometer, and a horizontal reflux condenser that was connected to a collection flask that was connected to a trap en route to a vacuum pump. When temperature reached 118° C., distillate was allowed to collect in the flask while the temperature continued to rise to 140° C. Vacuum was then gradually applied (to prevent surge of distillate) until full vacuum was obtained. At 170° C. and full vacuum, no more distillate was produced, with a total distillate collected at 623 g (99%). This clear, colorless distillate was confirmed to be 100% pure acetic acid.

During the whole process (ca., 4½ hrs. between the addition of reactants, hold period, heating and collecting), the product mix was colorless until about 80° C. when the product turned straw-colored. At 90° C., it turned light yellow and at 110° C., it looked yellow-orange (amber), while at 140° C. it was dark amber. The final product IPPA (residue) at 170° C. was a viscous, golden-yellow liquid and weighed 234 g.

$P^{31}$ NMR showed two main peaks: one single peak at delta 20.8 PPM (29%) and one single peak at delta 10.2 PPM (71%). These peaks correspond to isopropenyl phosphonic acid monomer (IPPA) ($C_3H_7O_3P$, 29%) and isopropenyl phosphonic acid anhydride dimer (IPPAA) ($C_6H_{12}O_5P_2$, 71%).

Example 2

Large-Scale Production of Isopropenylphosphonic Acid (IPPA)

Table 1 shows the amount of starting materials used to produce IPPA on large scale using $PCl_3$ as described in Example 3 of the '046 patent while Table 2 shows the amount of by-products that would be produced from this process. Table 3 shows the amounts of starting materials used to produce IPPA using the methods described herein. Table 4 indicates that the only by-product is glacial acetic acid, which can be recovered as 100% pure acetic acid and sold in the open market.

TABLE 1

| Raw Materials | Pounds | Mol. Wt | Moles | B.P. °C. | Gallons |
|---|---|---|---|---|---|
| Acetone | 1320 | 58.08 | 22.73 | 56.5 | 200 |
| Acetic Acid-Glacial | 6358 | 60.05 | 105.87 | 118 | 735 |
| PCl₃ | 3212 | 137.3 | 23.39 | 76 | 243 |
| Total | 10890 | | 152 | | 1178 |

TABLE 2

| Raw Materials | Pounds | Mol. Wt | Moles | B.P. °C. | Gallons |
|---|---|---|---|---|---|
| Hydrochloric Acid | 1136 | 36.46 | 28.85 | — | 362 |
| Acetyl Chloride | 3060 | 78.50 | 38.98 | 52 | 333 |
| Acetic Acid | 4019 | 60.05 | 28.86 | 118 | 465 |
| Total | 8215 | | 66.92 | | 1160 |

TABLE 3

| Raw Materials | Pounds | Mol. Wt | Moles | B.P. °C. | Gallons |
|---|---|---|---|---|---|
| Phosphorous Acid | 1918 | 82 | 23.39 | — | — |
| Acetic Anhydride | 4674 | 102 | 45.83 | 139 | 514 |
| Acetic Acid | 1871 | 60.05 | 31.16 | 118 | 216 |
| Acetone | 1638 | 58.08 | 28.21 | 56 | 248 |
| Total | 10101 | | | | 978 |

TABLE 4

| Raw Materials | Pounds | Mol. Wt | Moles | B.P. °C. | Gallons |
|---|---|---|---|---|---|
| Acetic Acid | 7136 | 60.05 | 118.8 | 118 | 825 |

The process used in the '046 patent produces 1,160 gallons of mixed hazardous materials (HCl and acetyl chloride in acetic acid and water) (Table 2). The acetyl chloride, HCl, and acetic acid cannot be separated in actual production. Conversely, use of the process described herein produces only glacial acetic acid (Table 4, 825 gallons), which can be recovered and sold in the open market. If one million pounds of IPPA were produced using the process in the '046 patent, theoretically 406,000 gallons of HCl, acetyl chloride, and acetic acid would be produced, which would create numerous environmental and safety issues. The use of the process described herein, however, theoretically produces 289,000 gallons of glacial acetic acid, which can be recovered and sold in the open market.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for making a compound, comprising admixing together compounds I, II, and III

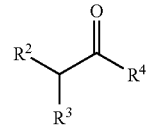

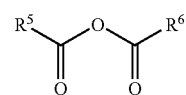

wherein $R^1$-$R^7$ comprises, independently, hydrogen, an alkyl group, a cycloalkyl group, a heterocycloalkyl group, an aryl group, a heteroaryl group, a protecting group, or a combination thereof, wherein compounds I, II and III react to produce a compound comprising the formula IV

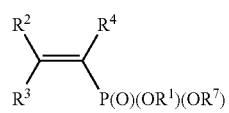

wherein $R^1$-$R^4$ and $R^7$ comprises, independently, hydrogen, an alkyl group, a cycloalkyl group, a heterocycloalkyl group, an aryl group, a heteroaryl group, a protecting group, or a combination thereof.

2. The method of claim 1, wherein $R^1$ and $R^7$ are hydrogen.

3. The method of claim 1, wherein $R^1$ and $R^7$ comprises, independently, methyl, ethyl, propyl, isopropyl, butyl, pentyl, or hexyl.

4. The method of claim 1, wherein $R^1$ and $R^7$ are methyl.

5. The method of claim 1, wherein $R^2$ is hydrogen and $R^4$ comprises a branched or straight chain alkyl group.

6. The method of claim 1, wherein $R^2$ and $R^3$ are hydrogen.

7. The method of claim 1, wherein $R^2$, $R^3$, and $R^4$ are hydrogen.

8. The method of claim 6, wherein $R^4$ comprises a branched- or straight-chain alkyl group.

9. The method of claim 8, wherein $R^4$ comprises ethyl, propyl, isopropyl, butyl, pentyl, or hexyl.

10. The method of claim 8, wherein $R^4$ comprises methyl.

11. The method of claim 6, wherein $R^4$ comprises an aryl group or a heteroaryl group.

12. The method of claim 6, wherein $R^4$ comprises a phenyl group.

13. The method of claim 1, wherein compound II comprises ethanal, methylphenyl ketone, or sulfonated benzyl methyl ketone.

14. The method of claim 1, wherein compound II comprises acetone.

15. The method of claim 1, wherein $R^5$ and $R^6$ comprises a branched- or straight-chain alkyl group.

16. The method of claim 1, wherein $R^5$ and $R^6$ comprises, independently, methyl, ethyl, propyl, isopropyl, butyl, pentyl, or hexyl.

17. The method of claim 1, wherein compound III comprises acetic anhydride, propionic anhydride, or butyric anhydride.

18. The method of claim 1, wherein compound I comprises phosphorous acid, compound II comprises acetone, and compound III comprises acetic anhydride.

19. The method of claim 1, wherein the reaction is conducted in the presence of an optional catalyst.

20. The method of claim 19, wherein the catalyst comprises $R^8COOH$, wherein $R^8$ comprises $C_1$-$C_8$ branched- or straight-chain alkyl.

21. The method of claim 20, wherein $R^8$ comprises methyl, ethyl, propyl, isopropyl, butyl, pentyl, or hexyl.

22. The method of claim 19, wherein the catalyst comprises acetic acid.

* * * * *